United States Patent
Crane et al.

(10) Patent No.: US 10,470,995 B2
(45) Date of Patent: Nov. 12, 2019

(54) MASCARA COMPOSITIONS COMPRISING A BIMODAL ACRYLIC POLYMER AND ANIONIC, WATER-DISPERSIBLE POLYESTER AND AN ALIPHATIC TACKIFIER

(71) Applicant: L'OREAL, Paris (FR)

(72) Inventors: Christine Marie Crane, Walnut Creek, CA (US); Angeles Clara Fonolla-Moreno, Rio de Janeiro (BR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/901,326

(22) Filed: Feb. 21, 2018

(65) Prior Publication Data
US 2019/0254950 A1   Aug. 22, 2019

(51) Int. Cl.
| | |
|---|---|
| *A61K 8/85* | (2006.01) |
| *A61Q 1/10* | (2006.01) |
| *A61K 8/81* | (2006.01) |
| *A61K 8/34* | (2006.01) |

(52) U.S. Cl.
CPC ............ *A61K 8/8152* (2013.01); *A61K 8/345* (2013.01); *A61K 8/85* (2013.01); *A61Q 1/10* (2013.01); *A61K 2800/30* (2013.01)

(58) Field of Classification Search
CPC ........ A61K 8/85; A61K 8/345; A61K 8/8152; A61Q 1/10
See application file for complete search history.

(56) References Cited

U.S. PATENT DOCUMENTS

| | | |
|---|---|---|
| 5,053,221 A | 10/1991 | Robertson et al. |
| 5,553,247 A | 9/1996 | Lallement |
| 5,985,258 A | 11/1999 | Alwattari et al. |
| 7,351,405 B2 | 4/2008 | De La Poterie |
| 2013/0028650 A1 | 1/2013 | Atis et al. |

FOREIGN PATENT DOCUMENTS

WO    01054660 A1    2/2002

OTHER PUBLICATIONS

"GNPD—Long Lash Waterproof Mascara", published on Feb. 20, 2018.

*Primary Examiner* — Zohreh A Fay
(74) *Attorney, Agent, or Firm* — Oblon, McClelland, Maier & Neustadt, L.L.P.

(57) ABSTRACT

A mascara composition includes a vehicle comprising water; a bimodal acrylic polymer including cationic functionality and anionic functionality; an anionic, water-dispersible polyester; and an aliphatic tackifier having a weight average molecular weight less than about 10,000 daltons. Methods of making up the eyelashes are also provided.

14 Claims, No Drawings

MASCARA COMPOSITIONS COMPRISING A BIMODAL ACRYLIC POLYMER AND ANIONIC, WATER-DISPERSIBLE POLYESTER AND AN ALIPHATIC TACKIFIER

FIELD OF THE INVENTION

The present invention relates to a cosmetic composition for keratinous materials such as keratin fibers. The cosmetic composition is preferably a mascara composition for eyelashes.

DISCUSSION OF THE BACKGROUND

Mascara compositions are commonly used to enhance the appearance of eyelashes. Conventional mascara compositions generally use waxes to form crystalline network structures to enhance curl, volume, length, thickness, and/or colors to eyelashes. However, conventional mascara compositions including waxes tend to become less resistant to oil and/or sebum, causing smearing, flaking, and/or color transferring after wearing for a certain amount of time.

The inventors of the present have found that certain mascara formulations are useful for enhancing one or more of ease of removal, gloss, as well as wear, curl, curl retention, and ease of application.

Accordingly, one aspect of the present invention is a mascara composition which is able to impart an enhanced appearance to the eyelashes by enhancing eyelash curling. Another aspect of the present invention is directed to a method of making up eyelashes to enhance physical appearance of the eyelashes.

SUMMARY OF THE INVENTION

According to certain embodiments of the present invention, a mascara composition includes a vehicle comprising water; a bimodal acrylic polymer including cationic functionality and anionic functionality; an anionic, water-dispersible polyester; and an aliphatic tackifier having a weight average molecular weight less than about 10,000 daltons.

According to certain other embodiments of the invention a method of making up eyelashes is provided. The method includes applying to said eyelashes the composition that includes a vehicle comprising water; a bimodal acrylic polymer including cationic functionality and anionic functionality; an anionic, water-dispersible polyester; and an aliphatic tackifier having a weight average molecular weight less than about 10,000 daltons.

DETAILED DESCRIPTION OF THE INVENTION

Unless otherwise indicated, all numbers expressing quantities of ingredients and/or reaction conditions are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, the expression "at least one" means one or more and thus includes individual components as well as mixtures/combinations. Other than in the operating examples, or where otherwise indicated, all numbers expressing quantities of ingredients and/or reaction conditions are to be understood as being modified in all instances by the term "about," meaning within 10% to 15% of the indicated number.

As used herein, the term "film-forming polymer" refers or "film forming agent" as used herein means a polymer or resin that leaves a film (e.g., a continuous film) on the substrate to which it is applied, for example, after a solvent accompanying the film former has evaporated, absorbed into and/or dissipated on or from the substrate.

As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

As used herein, "mascara" and "mascara composition" mean a composition that is intended to be applied to keratinous materials, preferably keratin fibers, in particular eyelashes and/or eyebrows, further in particular eyelashes.

As used herein, "keratinous materials" include, but are not limited to, skin, nail, living keratin fibers such as head hair, eyelashes, and eyebrows, and non-living keratin fibers such as swatches, extensions, and false eyelashes. The living and non-living keratin fibers include any mammalian hair, including human hair.

"Percent" or "%" as used herein, when referring to concentrations of ingredients or components in compositions refers to percent by weight. Unless otherwise stated, the percent is relative to the entire mascara composition.

"Solids basis" or "actives basis" refers to the amount of a particular ingredient exclusive of any solvents, carriers, impurities and the like that may be supplied with the particular ingredient "Substantially free" as used herein to refer to the presence of ingredients within compositions of the present invention, means that the particular ingredient is present in concentrations by weight of less than about 1%, such as less than about 0.5%, such as less than about 0.25%, such as about 0%.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "water-dispersible" means particles that are readily and uniformly separable throughout water such as on a scale of microns, tenths of microns, or hundredths of microns when blended therein, to form a stable mixture or 'dispersion.'

Mascara Composition

According to the present invention, the inventors have found that particular mascara compositions of the present invention have surprising and unexpected properties. These compositions include a bimodal acrylic polymer, an anionic, water-dispersible polyester; an aliphatic tackifier having a weight average molecular weight of less than about 10,000 daltons; a vehicle that includes water.

Bimodal Acrylic Polymer

Compositions of the present invention include a bimodal acrylic polymer. The term "bimodal" describes a polymer having both anionic functionality and cationic functionality. According to certain embodiments, the bimodal acrylic polymer forms a bimodal interpenetrating network containing cationic and anionic functionalities which is reversibly cross-linked at least partially through the multiple functionalities. Exemplary bimodal film forming agents are disclosed in POT patent application nos. WO 2005/087191 and WO 2006/028931, the entire contents of all of which are hereby incorporated by reference in their entireties.

One portion of the bimodal acrylic polymer contains anionic functionality such as from either methacrylic acid, acrylic acid, acrylate, methacrylate, or a combination thereof. The second portion of the bimodal polymer cationic functionality such as from simple amino esters of methacrylic acid or methacrylamide. The remaining monomer composition of the bimodal polymer may be comprised of lower alkyl (C1-C8) esters of both methacrylic and acrylic acid. The bimodal acrylic polymer may be formed by initiating a polymerization reaction in the presence of another polymer (e.g., polymerization of anionic monomers in the presence of a cationic polymer, or vice-versa), such as by free-radical polymerization in a water-based system.

Suitable bimodal acrylic polymers include, but are not limited to polymers comprising polyacrylates such as those identified in the *International Cosmetic Ingredient Dictionary and Handbook* (9$^{th}$ed. 2002) such as, for example, polyacrylate-1, polyacrylate-2, polyacrylate-3, polyacrylate-4 . . . polyacrylate-16, polyacrylate-17, polyacrylate-18, polyacrylate-21 . . . etc. Such (co)polymers, or similar (co)polymers, can be combined individually or with other (co)polymers in such a way to form suitable bimodal film forming agents having both cationic and anionic functionalities.

According to certain embodiments, the bimodal acrylic polymer comprises at least one monomer selected from acrylic acid, methacrylic acid, acrylate, methacrylate and combinations thereof and further comprises an amino ester of methacrylic acid or an amino ester of methacrylamide.

According to other embodiments, the bimodal film forming agent is selected from the group consisting of polymers consisting of polyacrylate-21 and acrylates/dimethylaminoethyl methacrylate copolymer (marketed under the name SYNTRAN PC 5100 by Interpolymer), polyacrylate-16 (marketed under the name SYNTRAN PC 5112 by Interpolymer), polyacrylate-18 and polyacrylate-19 (marketed under the name Syntran PC 5107 by Interpolymer), and polyacrylate-18 and polyacrylate-19 (marketed under the name Syntran PC 5117 by Interpolymer).

Notable examples of acrylic bimodal polymers in accordance with the present invention are a styrene/acrylates/ammonium methacrylate copolymer commercially available from Interpolymer Inc. of Canton, Mass. under the tradename SYNTRAN PC 5100; and Acrylates/Ethylhexyl Acrylate/HEMA Copolymer (And) Acrylates/Diethylaminoethyl Methacrylate/Ethylhexyl Acrylate Copolymer also commercially available from Interpolymer Inc., under the tradename SYNTRAN PC 5775.

The concentration of the bimodal acrylic polymers in the mascara may from about 2%, 3% or 4% by weight to about 8%, 12%, 15% or 20% by weight, including all combinations of such ranges, relative to the total weight of the mascara composition.

In certain embodiments of the invention, the film-forming polymer portion may include yet additional film-forming polymers that may be stabilized in the vehicle. Suitable additional film-forming polymers include, for example, any of various other acrylate and acrylic co-polymers, urethane polymers, polyesters and the like that are commonly used in mascara formulations.

Anionic, Water-Dispersible Polyester

Compositions of the present invention include an anionic, water-dispersible polyester. The anionic, water-dispersible polyester may be a reaction product of one or more compounds having a plurality of hydroxyl groups with one or more compounds having a plurality of carboxylic acid groups. In certain embodiments of the invention, the anionic, water-dispersible polyester is a sulfopolyester. In certain other embodiments of the invention, the anionic, water-dispersible polyester has a glass transition temperature from about 40° C. to about 55° C., such as from about 50° C. to about 55° C. In certain other embodiments, the anionic, water-dispersible polyester has a melt viscosity at 200 C that is from about 30,000 poise to about 50,000 poise.

One notable anionic, water-dispersible polyester is commercially available as Eastman AQ™ series sulfopolyesters, such as Eastman AQ™55S, from Eastman Chemical of Kingsport, Tenn.

The concentration of the anionic, water-dispersible polymers in the mascara may from about 0.5%, 1% or 5% by weight to about 5%, 10% or 20% by weight, including all combinations of such ranges, relative to the total weight of the mascara composition.

The bimodal acrylic polymer and the anionic, water dispersible polyester may be present in a ratio by weight from about 1 to about 2.5.

Aliphatic Tackifier

Compositions of the present invention include an aliphatic tackifier having a weight average molecular weight of less than about 10,000 daltons, such as less than about 5000 daltons, such as from about 1500 to about 4000. By "tackifier," it is meant a material that enhances surface adhesion and may have a glass transition temperature less than about 0° C. By "aliphatic" is meant a hydrocarbon based compounds or material that are straight, branched, or cyclic, but are free of aromatic ring structures.

The aliphatic tackifier may be a synthetic hydrocarbon polymer or based on hydrocarbon feedstocks. In certain notable embodiments, the aliphatic tackifier is unsaturated, such as a polybutene. Polybutene tackifiers may be made by polymerization of C4 olefins (e.g, primarily isobutene) and may be, for example, free-flowing, sticky with a honey-like consistency, or very tacky, semi-solid materials. Such synthetic hydrocarbon tackifiers may have a viscosity between about 1000 centistokes (cSt) and 5000 cSt when measured at 100° C. One notable aliphatic tackifier is INDOPOL H 1500, commercially available from Ineos Capital of London, England.

The concentration of the aliphatic hydrocarbon tackifier in the mascara may from about 0.25%, 0.5% or 1% by weight to about 2%, 5% or 10% by weight, including all combinations of such ranges, relative to the total weight of the mascara composition.

Wax

Compositions of the present invention may include wax. As used herein, "wax" is intended to mean a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C. or even as high as about 200° C.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

While in certain embodiments, compositions of the present invention include from about 1% to about 10% wax. However, in certain other embodiments, compositions of the present invention are substantially free of wax.

Polyhydric Alcohols

According to certain embodiments mascaras of the present invention include polyhydric alcohols such as glycerin or glycols such as propylene, butylene or hexylene glycol. The concentration of the polyhydric alcohols in the mascara may from about 1%, 2%, or 3% by weight to about 6%, 10% or 15% by weight, including all combinations of such ranges, relative to the total weight of the mascara composition.

Oil

Compositions of the present invention may additionally include oils. In certain particular embodiments, compositions of the present invention have less than 0.25% of waxes and less than 0.25% of oils.

As used herein, by "oils," it is meant compounds having a melting point of less than about 30 C and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others. In certain notable embodiments, the oils included in the compositions of the invention are silicone oils.

The concentration of oils in the mascara may from about 0.25%, 0.5% or 1% by weight to about 2%, 5% or 10% by weight, including all combinations of such ranges, relative to the total weight of the mascara composition.

Emulsifiers and Surfactants

According to certain embodiments of the present invention, the mascara composition may further optionally include emulsifiers and/or surfactants, primarily to assist in stabilizing oils in the composition and/or providing wetting or dispersing of the particulate portion. Any emulsifiers, surfactants, including anionic, nonionic, amphoteric, and cationic, emulsifiers or surfactants, may be used in the present invention, as long as the surfactant is cosmetically or dermatologically acceptable. In certain notable embodiments, the compositions include one or more non-ionic emulsifiers such as fatty acid esters of glycerol, ethoxylated fatty acids/esters, fatty alcohols and the like. The emulsifiers and surfactant may be used either singly or in combination two or more thereof. In one embodiment, the mascara composition may include an anionic surfactant/dispersant such as sodium laureth sulfate.

The concentration of emulsifiers and/or surfactants in the mascara may from about 0.25%, 0.5% or 3% by weight to about 5%, 10% or 15% by weight, including all combinations of such ranges, relative to the total weight of the mascara composition.

Colorants and Particulates

Mascara compositions of the present invention may optionally include at least one colorant. Suitable colorants include, but are not limited to inorganic particulates that impart color or optical effects and organic pigments. Particulate materials are generally finely divided particulates that are insoluble in but are otherwise homogeneously stabilized (suspended or dispersed) in a vehicle of the composition. The one or more particulate materials are typically materials that are incapable of chemically "self-fusing" in-use and are not themselves film-forming.

Suitable inorganic particulate materials include any of a variety of porous, semi-porous, non-porous, or hollow, coated or uncoated water-insoluble inorganic particulates such as silica, alumina, carbon and any of various oxides, silicates, aluminosilicates, nitrides, carbides, carbonates, and the like. In particular embodiments, the inorganic particulate is selected from carbon black, silica, and iron oxide. Other particulates, e.g., organic pigments such as lake pigments; other organic particulates such as polymeric particulates including nylon particulates, acrylate particulates (e.g., PMMA), silicone elastomer particulates, and the like may also be used.

Any of various lipophilic or water soluble dyes may be used as well. Typically, when the composition contains colorants, the composition may be used as a mascara composition. Alternatively, when the composition does not contain colorants, it is a clear or transparent composition which can be used as a basecoat (or topcoat) prior to (or after) application of a mascara composition to keratinous materials. A composition free of colorants may also be used as a solitary coating (without an additional separate basecoat or topcoat). However, it is possible that topcoats or basecoats could contain colorants, and/or that a mascara composition could contain little or no colorant.

The concentration of colorants in the mascara may from about 0.5%, 1% or 5% by weight to about 5%, 10% or 20% by weight, including all combinations of such ranges, relative to the total weight of the mascara composition.

Vehicle

In order to facilitate application to the eyelashes, mascaras of the present invention generally include a vehicle in which the other ingredients are stabilized (i.e., dissolved, dispersed, emulsified or suspended). The vehicle generally includes, consists or consists essentially of water. In certain embodiments of the invention, the mascara compositions of the present invention include at least about 30% water, such as from about 30% to about 80%, such as from about 35% to about 65%.

Additional Ingredients

The mascara composition of the present invention may further include various additives desirably used in cosmetic or dermatological compositions. For example, water, water-phase thickeners, oil-phase thickeners, dispersants, anti-oxidants, pH adjusters, preservatives, neutralizing agents, fragrances, fillers, co-solvents, plasticizers, cosmetic and dermatological active agents such as emollients, moisturizers, vitamins, UV filters, and sunscreens, and mixtures thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

Compositions of the present invention may be formulated having one or more distinct phases. In certain embodiments, the compositions include an aqueous (water) phase and in certain embodiments, the compositions include or further include a fatty phase that includes oils, waxes, and/or silicones. In certain notable embodiments, compositions of the present include a water phase and a fatty phase such as an oil or silicone phase.

According to certain embodiments, the mascara composition of the present invention is in the form of an emulsion.

The mascara composition of the present invention is intended to be applied onto keratinous materials such as keratin fibers, in particular, eyelashes or eyebrows. The way by which the mascara composition is applied onto the keratinous materials is not limited. Preferably, the mascara composition is applied onto keratin fibers by a brush, a wand, or a comb.

The compositions may be applied to eyelashes as needed, preferably once or twice daily, more preferably once daily and then preferably allowed to dry before subjecting to contact such as with clothing or other objects.

As described above, according to one aspect of the present invention, the mascara composition has improved cosmetic properties such as, for example, increased curl, improved curl retention, ease of removal, improved gloss, improved color, ease of application, and the like.

Methods of Making

Mascara compositions of the present invention may be made by mixing the anionic, water-dispersible polyester in water that has been heated, until dispersed and adding other suitable optional ingredients (e.g., colorants/pigments, preservatives, water soluble thickeners, water soluble emulsifiers, and plasticizers) into the water phase. Optional oil-soluble ingredients such as emulsifiers, oils and waxes may then be added. The composition may then be allowed to cool before adding the bimodal polymer and ingredients that may be temperature sensitive. The mixing may be accomplished by stirring, shaking, grounding, or beating, optionally with a stirrer, a magnetic stirrer, a shaker, a homogenizer, or any other methods suitably used to mix cosmetic composition. The mixing may be carried out with or without heating or cooling the ingredients.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective measurements.

Examples

Mascara compositions were prepared with the following classes of ingredients and corresponding approximate weight percentages, on an actives bases: 3% aliphatic tackifier, 10% pigment; 12% emulsifier/surfactant; 4% silicone oil; 2% silicone elastomer and silicone film forming polymer; 5% polyhydric alcohols; and about 4%-10%; thickeners, gellants, preservatives, filler and pH adjusters; and the remainder water (q.s.). The weight percentage of anionic acrylic polymer (SYNTRAN PC 5100 available from Interpolymer Inc. of Canton, Mass.) and anionic, water-dispersible polyester (Eastman AQ™55S, anionic water-dispersible polyester, available from Eastman Chemical of Kingsport, Tenn.) were varied according to the Table 1 below.

The compositions were tested for gloss. This was performed using a BYK Gardner micro glossmeter and following the ASTM Standard Test Method for determining Gloss. Gloss measurements were determined on 3.0 mil drawdowns of formulas on Laneta Black and White draw down cards. In this procedure, the products were scooped and spread evenly on the cards using a metal "drawdown" bar. Once the films dried (24 hours after application), the shine of the resulting films was measured on a BYK Gardner micro glossmeter. The measurements are reported in gloss units (GU) which represent the ratio of reflected to incident light of the films compared to that for a standard. Low gloss is a GU value of less than 10 GU at an angle of 60°. The result in Table below are an average of three trials.

The compositions were also tested for hardness. Experiments performed on a TA.XT Plus Texture Analyzer with a cylindrical TA-Delrin probe (10 mm diameter) in 6×2 cm stainless steel cups, filled with bulk at 25° C. Surface cut with stainless steel blade to ensure flat top surface. Settings: Test Mode: compression, Pre-test speed: 2 mm/sec, post-test speed: 2 mm/sec, test speed: 0.5 mm/sec, target mode: distance, distance: 5 mm, trigger force: auto, trigger force: 2 grams. After penetrating the sample, the probe returned to its initial position. A curve was generated—a plot of force (grams) as a function of time (seconds). When a 2 g surface trigger was attained the probe proceeds to penetrate to a depth of 5 mm. At this point (maximum force), the probe returns to its original position at constant speed (e.g. 2.0 mm/s). The maximum force (hardness, grams) reported below gives an indication of the softness of the sample (I. F. Alemeda, et. al., Intl. J. Pharma. 2006, 327, 73-77; H. Masmoudi, et al., Intl. J. Pharma. 2005, 289, 117-131). Experiments run in triplicate and the results averaged.

TABLE 1

|  | Wt. % Acrylic[1] | Wt. % Polyester[2] | Gloss 85° | Gloss 60° | Hardness |
| --- | --- | --- | --- | --- | --- |
| Ex. 1 | 0 | 10 | 16.6 | 45.1 | — |
| Ex. 2 | 2.4 | 0 | 3.6 | 21.6 | 7.8 |
| Ex. 3 | 4.8 | 2.5 | 10.5 | 42.9 | 26.4 |
| Ex. 4 | 6 | 0 | 11.0 | 41.3 | 23.9 |
| Ex. 5 | 4.8 | 7.5 | 21.8 | 53.8 | 50.3 |
| Ex. 6 | 7.2 | 0 | 6.4 | 29 | 69.8 |

[1]SYNTRAN PC 5100 available from Interpolymer Inc. of Canton, Massachusetts
[2]Eastman AQ ™55S, anionic water-dispersible polyester, available from Eastman Chemical of Kingsport, Tennessee (Polyester-5) available from AkzoNobel Surface Chemistry LLC Furthermore, similar mascara compositions were prepared with another bimodal acrylic polymer, (SYNTRAN PC5775 available from Interpolymer Inc. of Canton, Mass.) and anionic, water-dispersible polyester (Eastman AQ™55S, anionic water-dispersible polyester, available from Eastman Chemical of Kingsport, Tenn.) were varied according to the Table 2 below.

TABLE 2

|  | Wt. % Acrylic[1] | Wt. % Polyester[2] | Gloss 85° | Gloss 60° | Hardness |
| --- | --- | --- | --- | --- | --- |
| Ex. 1 | 11.64 | 0 | 24.2 | 5.0 | 50 |
| Ex. 2 | 3.88 | 0 | 7.5 | 2.0 | 9.05 |
| Ex. 3 | 11.64 | 7.5 | 36 | 23.6 | 52.74 |
| Ex. 4 | 11.64 | 10 | 48.3 | 26 | 43.98 |
| Ex. 5 | 5.82 | 7.5 | 19.2 | 8.7 | 19.00 |
| Ex. 6 | 9.7 | 2.5 | 32.1 | 7 | 12.80 |
| Ex. 7 | 3.88 | 10 | 29.6 | 12.4 | 29.31 |

[1]SYNTRAN PC 5775 available from Interpolymer Inc. of Canton, Massachusetts
[2]Eastman AQ ™55S, anionic water-dispersible polyester, available from Eastman Chemical of Kingsport, Tennessee (Polyester-5) available from AkzoNobel Surface Chemistry LLC The results indicate that anionic water-dispersible polyester can be used to dramatically increase gloss and reduce hardness of mascara compositions that include bimodal acrylic polymer.

What is claimed is:

1. A mascara composition comprising
a vehicle comprising water;
a bimodal acrylic polymer comprising a cationic functionality and anionic functionality; and
an anionic water-dispersible sulfopolyester; and
an aliphatic tackifier having a weight average molecular weight less than about 10,000 daltons.

2. The mascara composition of claim 1, further comprising a polyhydric alcohol.

3. The mascara composition of claim 1, wherein the composition is substantially free of wax.

4. The mascara composition of claim 1 further comprising from about by weight 0.25% to about 10% by weight of silicone oil.

5. The mascara composition of claim 1, wherein the aliphatic tackifier has a molecular weight less than about 5000 daltons.

6. The mascara composition of claim 1, wherein the aliphatic tackifier is unsaturated.

7. The mascara composition of claim 1, wherein the aliphatic tackifier is present in a concentration by weight of from about 1% to about 5%.

8. The mascara composition of claim 1, wherein the bimodal acrylic polymer is present in a concentration by weight of from about 2% to about 15%.

9. The mascara composition of claim 1, wherein the anionic, water dispersible sulfopolyester is present in a concentration by weight of from about 0.5% to about 20%.

10. The mascara composition of claim 1, wherein the bimodal acrylic polymer and the anionic, water dispersible sulfopolyester are present in a ratio by weight of bimodal acrylic polymer to anionic, water dispersible sulfopolyester that is from about 1:1 to about 2.5:1.

11. The mascara composition of claim 1, further comprising from about 0.5% by weight to about 20% by weight of colorants.

12. The mascara composition of claim 1, further comprising from about 0.25% by weight to about 15% by weight of emulsifiers and/or surfactants.

13. The mascara composition of claim 1, wherein the bimodal acrylic polymer comprises at least one monomer selected from acrylic acid, methacrylic acid, acrylate, methacrylate and combinations thereof and further comprises an amino ester of methacrylic acid or an amino ester of methacrylamide.

14. A method of making up eyelashes, comprising applying to said eyelashes the composition of claim 1.

* * * * *

UNITED STATES PATENT AND TRADEMARK OFFICE
CERTIFICATE OF CORRECTION

| | | |
|---|---|---|
| PATENT NO. | : 10,470,995 B2 | Page 1 of 1 |
| APPLICATION NO. | : 15/901326 | |
| DATED | : November 12, 2019 | |
| INVENTOR(S) | : Christine Marie Crane et al. | |

It is certified that error appears in the above-identified patent and that said Letters Patent is hereby corrected as shown below:

On the Title Page

Item (72), the Inventors' name:
"Christine Marie Crane, Walnut Creek, CA (US); Angeles Clara Fonolla-Moreno, Rio de Janeiro (BR)"

Should read:
--Christine Marie Crane, Walnut Creek, CA (US); Angeles Clara Fonolla-Moreno, Rio de Janeiro (BR); Omotayo Awofesobi, West Orange, NJ (US)--

Signed and Sealed this
Sixth Day of July, 2021

Drew Hirshfeld
*Performing the Functions and Duties of the
Under Secretary of Commerce for Intellectual Property and
Director of the United States Patent and Trademark Office*